United States Patent [19]

Hoffmann et al.

[11] Patent Number: 5,530,131

[45] Date of Patent: Jun. 25, 1996

[54] N-ALKYL-N'-POLY(OXYALKYL)-HEXAHYDROPYRIMIDINES

[75] Inventors: Herrmann Hoffmann; Gernot Kremer, both of Kelkheim, Germany

[73] Assignee: Hoechst Aktiengesellschaft, Germany

[21] Appl. No.: 243,577

[22] Filed: May 16, 1994

[30] Foreign Application Priority Data

May 15, 1993 [DE] Germany ............... P 43 16 374.2

[51] Int. Cl.[6] .................................................. C07D 239/04
[52] U.S. Cl. ........................................................... 544/335
[58] Field of Search ............................................... 544/335

[56] References Cited

U.S. PATENT DOCUMENTS

| | | | |
|---|---|---|---|
| 3,787,416 | 1/1974 | Cyba et al. | 544/335 |
| 4,281,126 | 7/1981 | Alink | 544/242 |
| 4,391,957 | 7/1983 | Becker | 528/62 |

FOREIGN PATENT DOCUMENTS 0070536  1/1983  European Pat. Off. .

Primary Examiner—John M. Ford
Attorney, Agent, or Firm—Connolly & Hutz

[57] ABSTRACT

The present invention relates to N-alkyl-N'-poly(oxyalkyl) hexahydropyrimidines of the formula I

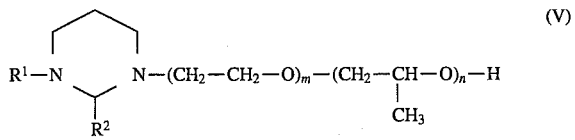

in which $R^1$ is $C_1$–$C_{30}$-alkyl or $C_2$–$C_{30}$-alkenyl, $R^2$ is hydrogen or $C_1$–$C_3$-alkyl, A is a 1,2-alkylene group having from 2 to 10, preferably from 2 to 5, carbon atoms and p is a number from 1 to 50.

The invention further provides for the use of N-alkyl-N'-poly(oxyalkyl)hexahydropyrimidines of the formula I as corrosion inhibitors in water/oil emulsions as are present in petroleum.

8 Claims, No Drawings

N-ALKYL-N'-POLY(OXYALKYL)-HEXAHYDROPYRIMIDINES

DESCRIPTION

Corrosion problems occur in all processes for petroleum extraction and petroleum processing in which iron or iron-containing metals come into contact with aqueous systems. Particularly serious are the problems with the action of salt water, carbon dioxide and hydrogen sulfide. However, the protective effect of the known commerical products—amines or quaternary ammonium compounds are usually used—is frequently insufficient or deteriorates after a short time, since the compounds are removed again from the metal surface to be protected by mechanical influences or reactions with aggressive media. The problem can seldom be solved by frequent further additions alone.

U.S. Pat. No. 3,787,416 describes N-hydroxyalkyl-N'-alkylhexahydropyrimidines and N-alkoxyalkyl-N'-alkyl-hexahydropyrimidines and also processes for the preparation thereof and use thereof. In these hexahydropyrimidines, the N atom preferably bears a $C_1$–$C_{10}$-alkyloxy-$C_1$–$C_{10}$-alkyl radical or a hydroxy-$C_1$–$C_{10}$-alkyl radical and the N' atom preferably bears a secondary $C_3$–$C_{40}$-alkyl radical or a $C_4$–$C_{12}$-cycloalkyl radical. The compounds described have a wide range of possible applications. They are used, inter alia, as additives for the preservation of organic substances, as crosslinking catalysts in urethane production, as intermediates in the production of pharmaceuticals and also as corrosion inhibitors in petroleum.

The danger of damaged plant by corrosion is particularly high when the composition of freshly extracted crude oil changes continually, e.g. if the well is flooded with salt water to increase the yield from the field, so that new, better corrosion protection agents having a long-term action are demanded. Furthermore, there is also a need for corrosion inhibitors which are dissolved or at least colloidally dispersed even in highly concentrated salt solutions.

It has now been found that use of N-alkyl-N'-poly(oxyalkyl)hexahydropyrimidines gives an excellent corrosion-protection action for water/oil emulsions as are present in petroleum, the long-term action in particular being improved in comparison with conventional corrosion inhibitors.

The invention provides N-alkyl-N'-poly(oxyalkyl)hexahydropyrimidines of the formula I

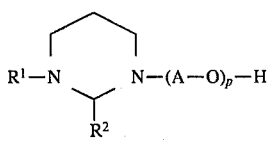

in which $R^1$ is $C_1$–$C_{30}$-alkyl or $C_2$–$C_{30}$-alkenyl, $R^2$ is hydrogen or $C_1$–$C_3$-alkyl, A is a 1,2-alkylene group having from 2 to 10, preferably from 2 to 5, carbon atoms and p is a number from 1 to 50.

Examples of straight-chain or branched alkyl and alkenyl groups $R^1$ which may be mentioned are: n-hexyl, n-heptyl, n-octyl, 2-ethylhexyl, n- and iso-nonyl, n- and iso-decyl, n-undecyl, n-dodecyl, n-tetradecyl, n-hexadecyl, n-octadecyl, oleyl, linoleyl and linolenyl.

Depending on the origin of the primary amine used in the synthesis of the compound I, $R^1$ is a radical of a naturally occurring fatty acid. Since the amines which are used in the synthesis of the compound I and in which $R^1$ is an alkyl or alkenyl group are generally random mixtures of homologs and also of isomers, it is advantageous to speak of an average number of carbon atoms in this radical $R^1$.

Preference is given to compounds I in which $R^1$ is an alkyl or alkenyl group having from 9 to 24 carbon atoms, in particular having from 10 to 18 carbon atoms. Particularly advantageous radicals $R^1$ are those which can be traced back to the $C_{10}$ fraction, the $C_{13}$ fraction, the $C_{10}/C_{12}$, the $C_{12}/C_{14}$, the $C_{13}/C_{15}$ or the $C_{16}/C_{18}$ fraction of a primary amine.

The 1,2-alkylene group A is, in particular, the ethylene group, besides also the propylene, 1,2-butylene and 2,3-butylene groups. Here, each group A can also be a random mixture of a plurality of the specified 1,2-alkylene groups, mixtures of ethylene and propylene units being preferred.

The degrees of alkoxylation p lie between 1 and 50, preferably from 3 to 35, in particular from 5 to 15. The values of p are usually averages.

The compounds of the formula I of the invention are generally obtained by alkoxylation of the N-substituted hexahydropyrimidines of the formula IV. The alkoxylation reagents used are epoxides such as ethylene oxide, propylene oxide, butylene oxide and 2,3-epoxy-1-propanol. The alkoxylation of the compounds of the formula IV is carried out by methods known per se. Suitable methods are known, for example, from J. March, Advanced Organic Chemistry, 2nd Edition, p. 357ff (1977).

If required, the compounds of the formula IV can be prepared according to the following synthesis scheme.

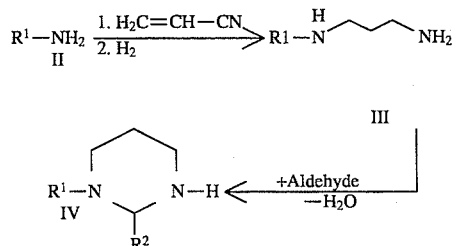

Starting materials for preparing the compounds of the formula IV are primary amines of the formula II. In so far as they are available, commercial primary amines are used. If the radicals $R^1$ are derived from naturally occurring fatty acids, these or the corresponding fats are used as starting materials for preparing the primary amines. For this purpose the fats are saponified, the fatty acids obtained are reduced to the nitriles and the corresponding primary fatty amines are obtained from the nitriles by hydrogenation. Reaction of the primary amine with acrylonitrile and subsequent hydrogenation gives the N-substituted propylenediamine of the formula III which, in a condensation reaction with the aldehyde with elimination of water, is converted to the N-substituted hexahydropyrimidine of the formula IV. The aldehydes used are formaldehyde and aldehydes having a $C_1$–$C_3$-alkyl group. Preferably, diamine of the formula III and aldehyde are reacted in equimolar amounts at temperatures in the range from 80° to 130° C. Advantageously, the diamine is initially charged and aldehyde is added dropwise, preferably in the form of a 35% by weight strength solution. During the addition, the water present is usually removed by distillation, advantageously by increasing the temperature, in general to up to 130° C. and, if desired, by applying a light vacuum (from 20 to 80 mbar) after the addition is complete. To avoid byproducts, in particular oxidation products, the preparation of the N-substituted hexahydropyrimidines of the formula IV is carried out under a stream of inert gas, preferably a stream of nitrogen. The N-substituted hexahydropyrimidines of the formula IV are generally obtained in good yield and with a high degree of purity and can be used for the subsequent alkoxylation without further purification.

A preferred group of compounds of the formula I is the hexahydropyrimidines which bear a chain comprising ethylene oxide/propylene oxide building blocks on the N' atom and have the formula V

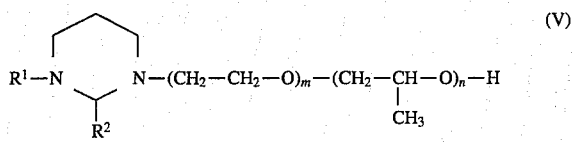

in which $R^1$ has the meaning specified above and m and n are identical or different and are numbers between 0 and 50, the sum of m and n being a number between 1 and 50.

The N-alkyl-N'-poly(oxyalkyl)hexahydropyrimidines of the formula I of the invention are suitable as corrosion inhibitors, in particular in petroleum extraction and processing plants which come into contact with salt water. The amounts of these compounds used as corrosion inhibitors are from 1 to 200, preferably from 1 to 50, mg per liter of corrosive liquid. Since the compounds of the invention are usually prepared as highly viscous liquids, they are in practice normally used as a 20–50% by weight strength solution, for example in water, glycols, glycol ethers, alcohols and other suitable solvents. These solutions can also include other corrosion-inhibiting active ingredients and also emulsifiers, antifoaming agents and further customary additives which improve the useful properties of the product being applied.

In general, however, the corrosion-inhibiting effect of such mixtures is produced by the corrosion-inhibitor components of the invention alone.

Preparative Examples

The determination of the degree of ethoxylation is carried out by titration of the basic nitrogen and by determination of the point at which turbidity sets in.

1. Preparation of N-tallowalkylhexahydropyrimidine 341 g (1.0 mol) of tallowpropylenediamine are initially charged and heated to 100° C. under a stream of nitrogen (about 5 l per hour). While stirring, 85.7 g (1.0 mol) of 35% strength formaldehyde solution are added dropwise, the water formed being simultaneously distilled off. After the addition is complete, water still present is distilled off until the internal temperature reaches about 130° C. To completely remove the water present, a light vacuum (about 20 mbar) is applied at this temperature for a period of about 2 hours. After cooling to room temperature, 350 g of an oily liquid are obtained. Amine number: 54.6 ml of 0.1N HCl/g (calculated: 53.9 ml of 0.1N HCl/g)

Water (by Karl Fischer method): 0.15% by weight

2. Alkoxylation of N-tallowalkylhexahydropyrimidine

The alkoxylation is carried out in two stages. In the first stage, 1 mol of ethylene oxide is added on without catalyst, in the second stage the material is additionally allowed to react further with ethylene oxide or propylene oxide under the action of a catalyst (NaOH) until the desired degree of conversion is reached.

First stage 1.0 mol of N-alkylhexahydropyrimidine from Example 1 are heated to 160° C. under a stream of nitrogen (1 bar). 48.4 g (1.1 mol) of ethylene oxide are metered in via a pressure burette over a period of 1 hour. After stirring further for 3 hours at 160° C., 390 g of the corresponding N-alkylhexahydropyrimidine ethoxylate are obtained.

Second stage 1.0 mol of the N-alkylhexahydropyrimidine ethoxylate from stage 1 are initially charged. After the introduction of 1.5 g of NaOH powder, a vacuum (20 mbar) is applied and water present is removed over a period of 1 hour at from 90° to 120° C. The desired amount of ethylene oxide is subsequently metered in at 160° C. If desired, the addition of propylene oxide is then carried out in a similar way. Table 1 shows the Examples 2 to 10 prepared.

TABLE 1

$R^1-N \underset{}{\bigcirc} N-(CH_2-CH_2-O)_m-(CH_2-CH(CH_3)-O)_n-H$ (V)

| Example | $R^1$ | m | n |
|---------|-------|---|---|
| 2 | $C_{16}/C_{18}$ | 4 | — |
| 3 | $C_{16}/C_{18}$ | 7 | — |
| 4 | $C_{16}/C_{18}$ | 10 | — |
| 5 | $C_{16}/C_{18}$ | 15 | — |
| 6 | $C_{16}/C_{18}$ | 20 | — |
| 7 | $C_{16}/C_{18}$ | 30 | — |
| 8 | $C_{16}/C_{18}$ | 7 | 3 |
| 9 | $C_{16}/C_{18}$ | 15 | 3 |
| 10 | $C_{16}/C_{18}$ | 15 | 6 |

The corrosion-inhibiting action is determined by two methods

1) Wheel test

The wheel test is a common method for testing corrosion inhibitors for the extraction of petroleum and natural gas. The test coupons selected are steel strips of unalloyed steel having dimensions of 130 mm×10 mm×1 mm. The test coupons are lightly sanded, degreased with acetone and weighed before and after the corrosion test. The test medium is salt water containing 5% by weight of NaCl, which is covered by a layer of 5% of kerosene. Both phases are saturated with $H_2S$ or $CO_2$.

10, 20 or 50 mg/l, based on the total volume of the liquid, of inhibitor are then added.

The degreased and weighed test coupons are subsequently introduced into this medium and subjected to mechanical movement (40 rpm by means of a shaft turning the test vessels) for 24 hours at 70° C.

The test strips are subsequently sanded, degreased with acetone and, after drying, weighed to determine the weight loss. The corrosion rates are given in mm/a (a=annum (year)). The blank value (test without addition of inhibitor) is determined for comparison. The tests using inhibitor are repeated at least once and the mean value of the corrosion rates calculated from the weight reduction is determined. The blank value given is the scattering range of 10 repeats.

The results of the wheel test are shown in Table 2.

2. Autoclave test

Use is made of a 4 l stirring autoclave, on to the stirrer shaft of which 8 steel coupons of 10 cm² are screwed on.

The following conditions are selected:
Medium: water containing 5% of NaCl and flushed with nitrogen until free of oxygen
Atmosphere: 10 bar of $CO_2$ or 2 bar of $H_2S$/4 bar of $CO_2$
Temperature: 120° C.
Time: 24 hours
Stirrer speed: 800 revolutions/min.
Measurement principle: weight loss
Corrosion rates: mm/a (mean value from 8 coupons)

The results of the autoclave test are shown in Table 3.

TABLE 2

Results of the wheel test

| Corrosion rates: | mm/a |
| Atmosphere: | $CO_2$ (1 bar) |
| Temperature: | 70° C. |
| Time: | 24 hours |
| Medium: | NaCl solution (5% by weight strength): kerosene (9:1), flushed with nitrogen until free of oxygen. |

| Example | mg/l | 4 mg/l | 20 mg/l |
| --- | --- | --- | --- |
| 2 | 0.30 | 0.25 | 0.17 |
| 3 | 0.25 | 0.18 | 0.16 |
| 4 | 0.21 | 0.17 | 0.16 |
| 5 | 0.23 | 0.19 | 0.16 |
| 6 | 0.33 | 0.22 | 0.18 |

TABLE 2-continued

| 7 | 0.35 | 0.18 | 0.20 |
| 8 | 0.39 | 0.33 | 0.22 |
| 9 | 0.30 | 0.30 | 0.19 |
| 10 | 0.29 | 0.23 | 0.19 |
| Coconutdimethylbenzyl-ammonium chloride (comparison) | 0.35 | 0.30 | 0.30 |
| Blank value | 0.70–0.85 | | |

TABLE 3

Results of the autoclave test

| Example | 10 bar $CO_2$/120° C. | 2 bar $H_2S$/4 bar $CO_2$/120° C. |
| --- | --- | --- |
| 2 | 1.95 ± 0.20 mm/a | 0.35 ± 0.05 mm/a |
| 3 | 1.21 ± 0.15 mm/a | 0.37 ± 0.03 mm/a |
| 4 | 0.95 ± 0.15 mm/a | 0.20 ± 0.02 mm/a |
| 5 | 1.35 ± 0.23 mm/a | 0.54 ± 0.03 mm/a |
| 6 | 1.31 ± 0.06 mm/a | 0.34 ± 0.06 mm/a |
| 7 | 1.53 ± 0.09 mm/a | 0.46 ± 0.04 mm/a |
| 8 | — | — |
| 9 | 1.70 ± 0.33 mm/a | — |
| 10 | — | — |
| Amidoamine from 2 mol of napthenic acid + 1 mol of diethylenetriamine (comparison) | 3.7 ± 0.3 mm/a | 0.51 ± 0.06 mm/a |
| Coconutdimethylbenzyl-ammonium chloride (comparison) | 2.3 ± 0.17 mm/a | 0.80 ± 0.05 mm/a |
| Blank value | 10.7 ± 1.2 mm/a | 4.8 ± 0.5 mm/a |

| | | Solubility at RT, assessed after 24 h, sample 40% active ingredient in butyl glycol | | | | | | | |
| --- | --- | --- | --- | --- | --- | --- | --- | --- | --- |
| Ex. | Concentration | in water | 1% NaCl | 3% NaCl | 5% NaCl | 8% NaCl | 10% NaCl | 15% NaCl | in salt water** |
| 2* | 0.1% | tr. turb. | tr. turb. | tr. turb. | tr. turb. | tr. turb. | tr. turb. | — | tr. turb. |
| | 1% | tr. turb. | tr. turb. | tranap. | tranap. | tranap. | tranap. | — | emulsion |
| | 5% | transp. | emulsion | emulsion | ph. sep. | ph, sep. | ph. sep. | — | — |
| | 10% | transp. | ph. sep. | ph. sep. | ph. sep. | ph. sep. | ph. sep. | — | — |
| 3* | 0.1% | clear | clear | clear | clear | clear | clear | clear | clear |
| | 1% | clear | clear | clear | clear | clear | clear | tr. turb. | clear |
| | 5% | clear | clear | tr. turb. | tr. turb. | tr. turb. | emulsion | ph. sep. | — |
| | 10% | clear | clear | tr. turb. | tr. turb. | tr. turb. | ph. sep, | — | — |
| 4 | 0.1% | clear | clear | clear | clear | clear | — | — | — |
| | 1% | tr. turb. | transp. | transp. | transp. | transp. | — | — | — |
| | 5% | tr. turb. | transp. | transp. | ph. sep. | — | — | — | — |
| | 10% | tr. turb. | clear | clear | ph. sep. | — | — | — | — |
| 5* | 0.1% | clear | clear | clear | clear | clear | clear | clear | clear |
| | 1% | clear | clear | clear | clear | clear | clear | tr. turb. | clear |
| | 5% | clear | clear | clear | clear | tr. turb. | tr. turb. | transp. | emulsion |
| | 10% | clear | clear | clear | transp. | emulsion | emulsion | ph. sep. | — |
| 6 | 0.1 % | clear | clear | clear | clear | clear | clear | clear | — |
| | 1% | clear | clear | clear | clear | clear | clear | clear | — |
| | 5% | clear | clear | clear | clear | clear | clear | clear | — |
| | 10% | clear | clear | clear | clear | clear | clear | ph. sep. | — |
| 7 | 0.1 % | clear | clear | clear | clear | clear | clear | clear | — |
| | 1% | clear | clear | clear | clear | clear | clear | clear | — |
| | 5% | clear | clear | clear | clear | clear | clear | ph. sep. | — |
| | 10% | clear | clear | emulsion | emulsion | ph. sep. | ph. sep. | ph. sep. | — |
| 8 | 0.1% | clear | clear | clear | clear | — | — | — | — |
| | 1% | tr. turb. | transp. | transp. | ph. sep. | — | — | — | — |
| | 5% | ph. sep. | ph. sep. | ph. sep. | ph. sep. | — | — | — | — |

| | Solubility at RT, assessed after 24 h, sample 40% active ingredient in butyl glycol | | | | | | | |
|---|---|---|---|---|---|---|---|---|
| Ex. | Concentration | in water | 1% NaCl | 3% NaCl | 5% NaCl | 8% NaCl | 10% NaCl | 15% NaCl | in salt water** |
| | 10% | ph. sep. | ph. sep. | ph. sep. | ph. sep. | — | — | — | — |
| 9 | 0.1% | clear | clear | clear | clear | — | — | — | — |
| | 1% | tr. turb. | tr. turb. | tr. turb. | ph. sep. | — | — | — | — |
| | 5% | emulsion | ph. sep. | ph. sep. | ph. sep. | — | — | — | — |
| | 10% | emulsion | ph. sep. | ph. sep. | ph. sep. | — | — | — | — |
| 10 | 0.1% | clear | clear | clear | clear | — | — | — | — |
| | 1% | clear | clear | clear | clear | — | — | — | — |
| | 5% | emulsion | ph. sep. | ph. sep. | ph. sep. | — | — | — | — |
| | 10% | ph. sep. | ph. sep. | ph. sep. | ph. sep. | — | — | — | — | ph. sep. = phase separation
turb. = turbid, i.e. light milky turbidity
tr. turb. = trace of turbidity
*were concentrated using rotary evaporators
Example 2: 91.5%
Example 3: 91.5%
Example 5: 94.0%
**7% NaCl
2% CaCl$_2$.2H$_2$O
1% MgCl.6H$_2$O

We claim:

1. An N-alkyl-N'-poly(oxyalkyl)hexahydropyrimidine of the formula I

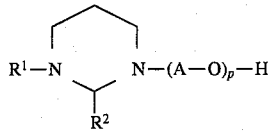

in which $R^1$ is $C_1$–$C_{30}$-alkyl or $C_2$–$C_{30}$-alkenyl, $R^2$ is hydrogen or $C_1$–$C_3$-alkyl, A is a 1,2-alkylene group having from 2 to 10 carbon atoms and p is a number from 3 to 50.

2. A compound of the formula I as claimed in claim 1, wherein $R^1$ is $C_9$–$C_{24}$-alkyl, or $C_9$–$C_{24}$-alkenyl.

3. An N-alkyl-N'-poly(oxyalkyl)hexahydropyrimidine of the formula V

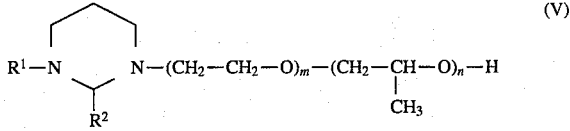

in which $R^1$ is $C_1$–$C_{30}$-alkyl or $C_2$–$C_{30}$-alkenyl, $R^2$ is hydrogen or $C_1$–$C_3$-alkyl, m is a number between 0 and 50, n is a number between 0 and 50, the sum of m and n being a number between 4 and 50.

4. The compound as claimed in claim 3, wherein m is a number between 4 and 50 and the sum of m and n being a number between 4 and 50.

5. A compound of the formula I as claimed in claim 1, wherein A is an alkylene group having from 2 to 5 carbon atoms.

6. A compound of the formula I as claimed in claim 5, wherein p is a number from 3 to 35.

7. A compound of the formula I as claimed in claim 1, wherein p is a number from 3 to 35.

8. A compound of the formula I as claimed in claim 1, wherein $R^1$ is $C_{10}$–$C_{18}$-alkyl or $C_{10}$–$C_{18}$-alkenyl.

* * * * *